(12) United States Patent  
Wakui (10) Patent No.: US 10,330,583 B2  
(45) Date of Patent: Jun. 25, 2019

(54) CELL IMAGING APPARATUS AND METHOD FOR GENERATING A COMPOSITE IMAGE

(71) Applicant: FUJIFILM Corporation, Tokyo (JP)

(72) Inventor: Takashi Wakui, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 11 days.

(21) Appl. No.: 15/437,806

(22) Filed: Feb. 21, 2017

(65) Prior Publication Data

US 2017/0167965 A1 Jun. 15, 2017

Related U.S. Application Data

(63) Continuation of application No. PCT/JP2015/076206, filed on Sep. 16, 2015.

(30) Foreign Application Priority Data

Sep. 30, 2014 (JP) ................. 2014-200739

(51) Int. Cl.
*C12Q 1/02* (2006.01)
*G06K 9/00* (2006.01)
(Continued)

(52) U.S. Cl.
CPC .......... *G01N 15/1456* (2013.01); *C12Q 1/02* (2013.01); *G01N 15/1429* (2013.01);
(Continued)

(58) Field of Classification Search
None
See application file for complete search history.

(56) References Cited

U.S. PATENT DOCUMENTS

2003/0216646 A1\* 11/2003 Angelsen ................. A61B 8/06  
600/437  
2005/0177054 A1\* 8/2005 Yi ........................ A61B 5/055  
600/510

(Continued)

FOREIGN PATENT DOCUMENTS

EP 3 076 219 A1 10/2016  
JP 2007-121106 A 5/2007  
(Continued)

OTHER PUBLICATIONS

Japanese Notification of Reasons for Refusal dated Jun. 27, 2017 for Japanese Patent Application No. 2014-200739.

(Continued)

*Primary Examiner* — Dowu O Osifade  
(74) *Attorney, Agent, or Firm* — Birch, Stewart, Kolasch & Birch, LLP (57) ABSTRACT

There is provided a cell imaging apparatus and method capable of generating a high-quality composite image as an image to be evaluated. The cell imaging apparatus includes: an imaging unit 10 that images a cell group including a plurality of periodically moving cells while changing an imaging range; a phase information acquisition unit 21 that acquires information based on the timing of the same phase in each period of the periodic movement; and a composite image generation unit 22 that generates a composite image by arranging images of the respective imaging ranges. The imaging unit 10 captures images with the same phase for the respective imaging ranges on the basis of the information based on the timing of the same phase, and the composite image generation unit 22 generates the composite image by arranging the images with the same phase.

16 Claims, 7 Drawing Sheets

(51) Int. Cl.

| | |
|---|---|
| *G01N 15/00* | (2006.01) |
| *G01N 15/10* | (2006.01) |
| *G01N 15/14* | (2006.01) |
| *G02B 21/36* | (2006.01) |
| *H04N 5/225* | (2006.01) |
| *H04N 5/445* | (2011.01) |
| *G01N 33/483* | (2006.01) |

(52) U.S. Cl.
CPC ..... *G01N 15/1434* (2013.01); *G01N 15/1468* (2013.01); *G01N 33/4833* (2013.01); *G02B 21/367* (2013.01); *G06K 9/00134* (2013.01); *G06K 9/00147* (2013.01); *G06K 9/00536* (2013.01); *H04N 5/44504* (2013.01); *G01N 2015/0065* (2013.01); *G01N 2015/1006* (2013.01); *G01N 2015/144* (2013.01); *H04N 5/225* (2013.01)

(56) References Cited

U.S. PATENT DOCUMENTS

| | | |
|---|---|---|
| 2013/0070971 A1 | 3/2013 | Kunihiro et al. |
| 2015/0146081 A1 | 5/2015 | Oshima et al. |

FOREIGN PATENT DOCUMENTS

| | | |
|---|---|---|
| JP | 2008-76088 A | 4/2008 |
| WO | WO 2011/122200 A1 | 10/2011 |
| WO | WO 2013/183233 A1 | 12/2013 |
| WO | WO 2015/104763 A1 | 7/2015 |

OTHER PUBLICATIONS

International Search Report for PCT/JP2015/076206 dated Dec. 22, 2015.
Written Opinion of the International Searching Authority for PCT/JP2015/076206 (PCT/ISA/237) dated Dec. 22, 2015.
Extended European Search Report for corresponding European Application No. 15846168.1, dated Nov. 7, 2017.
International Preliminary Report on Patentability and English translation of Written Opinion of the International Searching Authority dated Apr. 4, 2017, issued in PCT/JP2015/076206 (Forms PCT/IB/373 and PCT/ISA/237).
European Office Action for corresponding European Application No. 15846168.1, dated Mar. 5, 2019.

\* cited by examiner

AT TIME OF CONTRACTION

MYOCARDIAL CELL

AT TIME OF RELAXATION

FIG. 16

CELL IMAGING APPARATUS AND METHOD FOR GENERATING A COMPOSITE IMAGE

CROSS-REFERENCE TO RELATED APPLICATIONS

This application is a Continuation of PCT International Application No. PCT/JP2015/076206 filed on Sep. 16, 2015, which claims priority under 35 U.S.C § 119(a) to Japanese Patent Application No. 2014-200739 filed on Sep. 30, 2014. Each of the above application(s) is hereby expressly incorporated by reference, in its entirety, into the present application.

BACKGROUND OF THE INVENTION

1. Field of the Invention

The present invention relates to a cell imaging apparatus and method for imaging a cell group including a plurality of periodically moving cells.

2. Description of the Related Art

In recent years, regenerative medicine for performing treatment by culturing specific cells, such as myocardium, skin, or large intestine, in a sheet form and transplanting these into a patient has been drawing attention.

When producing a cell sheet, such as myocardium, first, a small amount of cells are collected from the living body, the collected cells are induced to undifferentiated cells, such as iPS cells, and the obtained undifferentiated cells are cultured. Then, the obtained cells are induced to differentiate into myocardial cells, and the differentiated myocardial cells are arranged in a sheet form and are cultured. In this manner, a cell sheet is produced.

In the process of culturing the cells arranged in a sheet form as described above, visual observation using a microscope and evaluation are performed to check abnormalities. In the future, however, it is conceivable that such evaluation is automatically performed with the spread of regenerative medicine.

As a method for automatically evaluating the quality, abnormalities, or the like of a cell sheet, for example, a method of capturing an image of a cell sheet using a microscope and acquiring and evaluating the feature quantity of the image can be considered.

In the case of performing evaluation based on an image obtained by imaging cells, for example, in the case of a small amount of cells, the cells can be contained within the imaging range of one field of view. However, in the case of cells arranged in a sheet form as described above, the cells cannot be contained within the imaging range of one field of view. Accordingly, imaging is performed a plurality of times in multiple fields of view. Then, captured images obtained by performing imaging of a plurality of times as described above are arranged side by side to generate one composite image.

SUMMARY OF THE INVENTION

Figure 15:
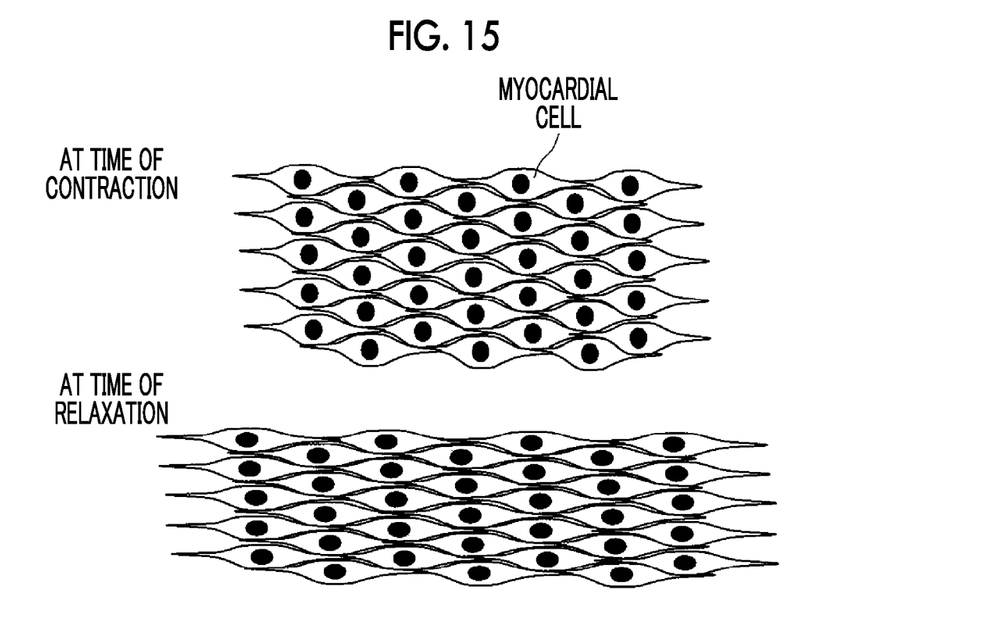
FIG. 15 is a diagram schematically showing a state when myocardial cells contract and a state when myocardial cells are relaxed.

Here, when generating one composite image from a plurality of captured images as described above, for example, in a case where cells to be imaged are periodically moving cells, such as myocardial cells or large intestine cells, the phase of the periodic movement may differ at the time of imaging each imaging range. For example, myocardial cells differ in shape depending on the phase of pulsation. The upper diagram of FIG. 15 schematically shows a state when myocardial cells contract, and the lower diagram of FIG. 15 shows a state when myocardial cells are relaxed.

Figure 16:
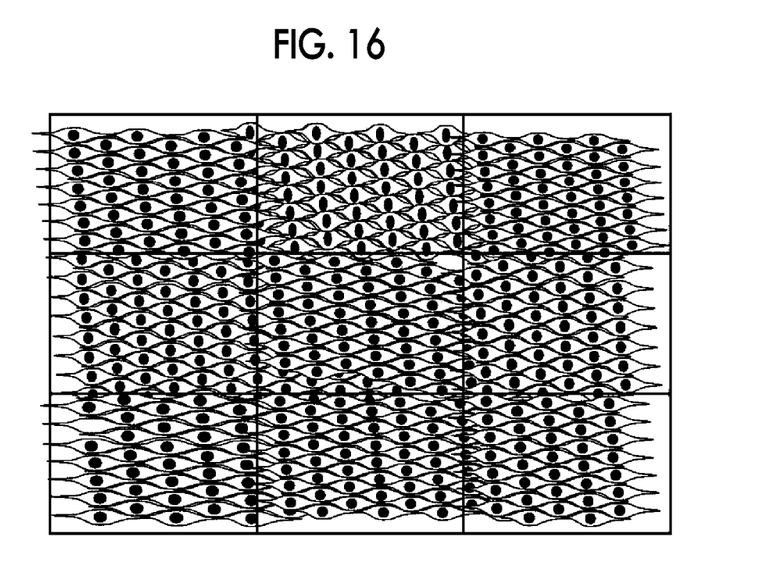
FIG. 16 is a diagram showing an example of a composite image obtained by tiling a plurality of captured images with different phases.

Therefore, in a case where captured images of imaging ranges having different phases are arranged side by side, as shown in FIG. 16, it is not possible to match the shapes of cells at the joint, and even an image to be evaluated becomes a poor-quality composite image.

JP2008-76088A proposes performing matching between adjacent captured images when arranging a plurality of captured images side by side. However, the periodic movement of cells described above has not been taken into consideration.

WO2011/122200A discloses a method for evaluating the pulsation of myocardial cells, but there is no description about so-called tiling for arranging a plurality of images side by side that has been described above.

In view of the aforementioned problem, it is an object of the present invention to provide a cell imaging apparatus and method capable of generating a high-quality composite image as an image to be evaluated by matching the shapes of cells at the joint when generating one composite image by imaging a group of periodically moving cells in a plurality of imaging ranges and arranging the plurality of captured images side by side.

A cell imaging apparatus of the present invention comprises: an imaging unit that images a cell group including a plurality of periodically moving cells while changing an imaging range; a phase information acquisition unit that acquires information based on a timing of the same phase in each period of the periodic movement; and a composite image generation unit that generates a composite image by arranging images of the respective imaging ranges. The imaging unit captures images with the same phase for the respective imaging ranges on the basis of the information based on the timing of the same phase, and the composite image generation unit generates the composite image by arranging the images with the same phase.

In the cell imaging apparatus of the present invention, it is possible to comprise an in-phase timing receiving unit that receives a setting input of a timing of the same phase.

In a case where the cell group is a myocardial cell group, a pulsation detection unit that detects a pulsation, which is periodic movement of the myocardial cell group, can be provided, and the phase information acquisition unit can acquire the information, which is based on the timing of the same phase, based on information of the pulsation.

The imaging unit can perform imaging of a plurality of times for each imaging range before capturing the images with the same phase, and the phase information acquisition unit can acquire the information, which is based on the timing of the same phase, based on images acquired by the plurality of imaging operations.

In a case where the cell group is a myocardial cell group, the phase information acquisition unit can acquire a contraction timing or a relaxation timing in pulsation of the myocardial cell group.

The phase information acquisition unit can acquire both the contraction timing and the relaxation timing, the imaging unit can capture an image at both the contraction timing and the relaxation timing for each imaging range, and the composite image generation unit can generate a first composite image by arranging images at the contraction timing of each imaging range and generate a second composite image by arranging images at the relaxation timing of each imaging range.

The imaging unit can determine an imaging timing of the image based on information regarding a predetermined movement time for movement between the imaging ranges adjacent to each other and the information regarding the timing of the same phase.

A cell imaging apparatus of the present invention comprises: an imaging unit that images a cell group, which includes a plurality of periodically moving cells, a plurality of times for each imaging range while changing an imaging range; an image selection unit that selects images with the same phase in each period of the periodic movement from a plurality of images acquired by a plurality of imaging operations in each imaging range; and a composite image generation unit that generates a composite image by arranging the images with the same phase selected by the image selection unit.

In the cell imaging apparatus of the present invention described above, it is possible to comprise an in-phase information receiving unit that receives designation of the same phase in each period of the periodic movement.

In a case where the cell group is a myocardial cell group, it is possible to comprise a pulsation detection unit that detects a pulsation that is periodic movement of the myocardial cell group, and the image selection unit can select the images with the same phase based on information of the pulsation.

The image selection unit can select the images with the same phase based on images acquired by the plurality of imaging operations.

In a case where the cell group is a myocardial cell group, the image selection unit can select an image captured at a contraction timing or an image captured at a relaxation timing in pulsation of the myocardial cell group.

The image selection unit can select both an image captured at the contraction timing and an image captured at the relaxation timing for each imaging range, and the composite image generation unit can generate a first composite image by arranging images at the contraction timing of each imaging range, and can generate a second composite image by arranging images at the relaxation timing of each imaging range.

A cell imaging method of the present invention is a cell imaging method for imaging a cell group including a plurality of periodically moving cells while changing an imaging range. The cell imaging method includes: acquiring information based on a timing of the same phase in each period of the periodic movement; capturing images with the same phase for the respective imaging ranges on the basis of the information based on the timing of the same phase, and generating a composite image by arranging the images with the same phase of the respective imaging ranges.

The cell imaging method of the present invention can include: imaging a cell group, which includes a plurality of periodically moving cells, a plurality of times for each imaging range while changing an imaging range; selecting images with the same phase in each period of the periodic movement from a plurality of images acquired by a plurality of imaging operations in each imaging range; and generating a composite image by arranging the selected images with the same phase.

According to the cell imaging apparatus and method of the present invention, when imaging a cell group including a plurality of periodically moving cells while changing the imaging range, information based on the timing of the same phase in each period of the periodic movement is acquired, images with the same phase are captured for the respective imaging ranges on the basis of the information based on the timing of the same phase, and a composite image is generated by arranging the images with the same phase of the respective imaging ranges. Therefore, since it is possible to match the shapes of cells at the joint of adjacent images, it is possible to generate a high-quality composite image as an image to be evaluated.

According to the cell imaging apparatus and method of the present invention, a cell group including a plurality of periodically moving cells is imaged a plurality of times for each imaging range while changing the imaging range, images with the same phase in each period of the periodic movement are selected from a plurality of images acquired by a plurality of imaging operations in each imaging range; and a composite image is generated by arranging the selected images with the same phase. Therefore, since it is possible to match the shapes of cells at the joint of adjacent images, it is possible to generate a high-quality composite image as an image to be evaluated.

DESCRIPTION OF THE PREFERRED EMBODIMENTS

Figure 1:
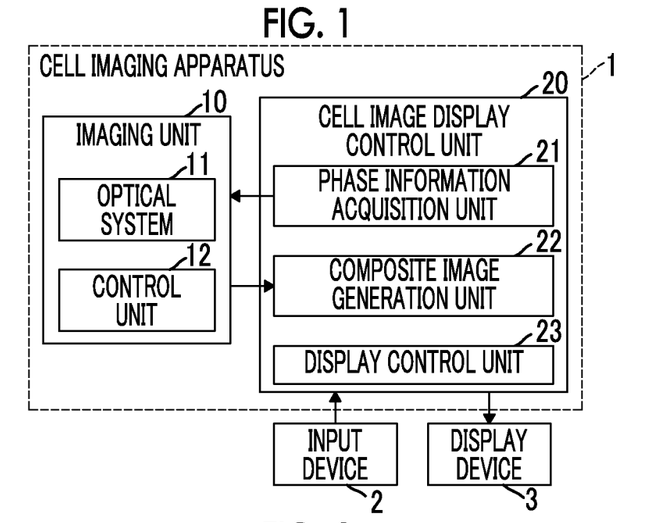
FIG. 1 is a block diagram showing the schematic configuration of a cell imaging display system using a first embodiment of a cell imaging apparatus of the present invention.

Hereinafter, a cell imaging display system using a first embodiment of a cell imaging apparatus and method of the present invention will be described in detail with reference to the diagrams. FIG. 1 is a block diagram showing the schematic configuration of the cell imaging display system using the cell imaging apparatus of the present embodiment.

As shown in FIG. 1, the cell imaging display system of the present embodiment includes a cell imaging apparatus 1, an input device 2, and a display device 3.

The cell imaging apparatus 1 includes an imaging unit 10 that images a cell group including a plurality of periodically moving cells while sequentially changing the imaging range and a cell image display control unit 20 that generates a composite image by combining captured images of respective imaging ranges, which are captured by the imaging unit 10, and displays the composite image. As a cell group of periodically moving cells, there is a myocardial cell group including myocardial cells that periodically move by pulsation, a large intestine cell group including large intestine cells, or the like.

The imaging unit 10 includes an optical system 11 and a control unit 12. The optical system 11 includes a microscope for capturing a phase difference image, a bright field image, a differential interference image, or a fluorescence image of a cell group. The optical system 11 includes an imaging element, such as a complementary metal-oxide semiconductor (CMOS) sensor or a charge-coupled device (CCD) sensor, and a captured image that is captured by the imaging element is output to the cell image display control unit 20. As a configuration for capturing the phase difference image, the bright field image, the differential interference image, or the fluorescence image, it is possible to use a known configuration.

The control unit 12 controls the entire imaging unit 10. Specifically, the control unit 12 of the present embodiment controls the operation, optical magnification, and the like of the imaging element of the optical system 11. In particular, the control unit 12 of the present embodiment controls the imaging timing of the imaging element, and the imaging timing is controlled based on the timing acquired by a phase information acquisition unit 21 to be described later. A specific method of controlling the imaging timing of an imaging element will be described in detail later.

Figure 2:
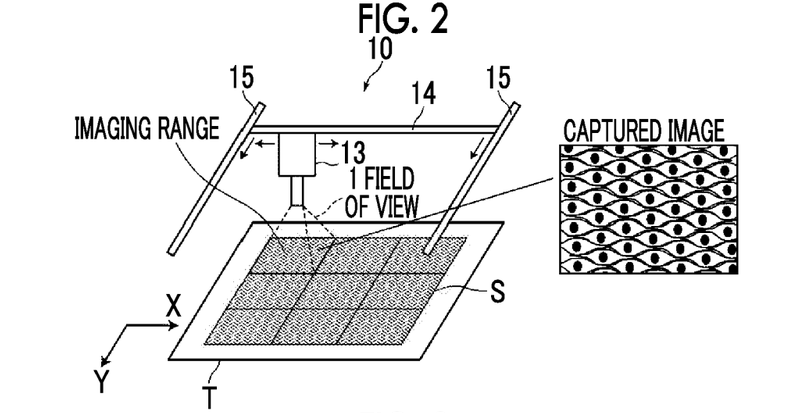
FIG. 2 is a perspective view showing the schematic configuration of an imaging unit.

FIG. 2 is a perspective view showing the schematic configuration of the imaging unit 10. As shown in FIG. 2, the optical system 11 and the control unit 12 described above are housed in a casing of an imaging unit main body 13, and the imaging unit 10 includes an X direction transport unit 14 and a Y direction transport unit 15 to move the imaging unit main body 13. The X direction transport unit 14 transports the imaging unit main body 13 in an X direction, and the Y direction transport unit 15 transports the X direction transport unit 14 in a Y direction perpendicular to the X direction. Each of the X direction transport unit 14 and the Y direction transport unit 15 is configured to include a transport mechanism, a driving motor for driving the transport mechanism, and the like. As a specific configuration, it is possible to use a known configuration. The control unit 12 also controls the operations of the X direction transport unit 14 and the Y direction transport unit 15.

As shown in FIG. 2, the imaging unit 10 images a cell group S placed on a stage T provided on a side below the X direction transport unit 14 and the Y direction transport unit 15. The imaging unit 10 captures an image while sequentially changing the imaging range on the cell group S by moving the imaging unit main body 13 in the X and Y directions using the X direction transport unit 14 and the Y direction transport unit 15 so that the field of view of the imaging unit main body 13 is sequentially changed. In addition, FIG. 2 schematically shows an imaging range (range indicated by a thick solid line) imaged in one field of view of the imaging unit main body 13. In addition, FIG. 2 shows an example of a captured image in one imaging range.

Although only the imaging range of three rows by three columns is shown in FIG. 2, the number of imaging ranges is determined, in practice, from the size of the cell group S to be imaged and the size of the imaging range of one field of view. The size of the cell group S to be imaged is, for example, several square centimeter to tens of square centimeter in a case where the cell group S is a myocardial sheet including a myocardial cell group. The size of the imaging range of one field of view is, for example, several hundreds of square micrometer in a case where the optical magnification is 10 to 20 times.

In the present embodiment, a microscope is used as the optical system 11 in the imaging unit 10. However, capturing an image of a group of cells is not limited to the microscope, and an image of each imaging range may be captured by scanning using a line sensor, for example.

Referring back to FIG. 1, the cell image display control unit 20 includes the phase information acquisition unit 21, a composite image generation unit 22, and a display control unit 23.

Figure 3:
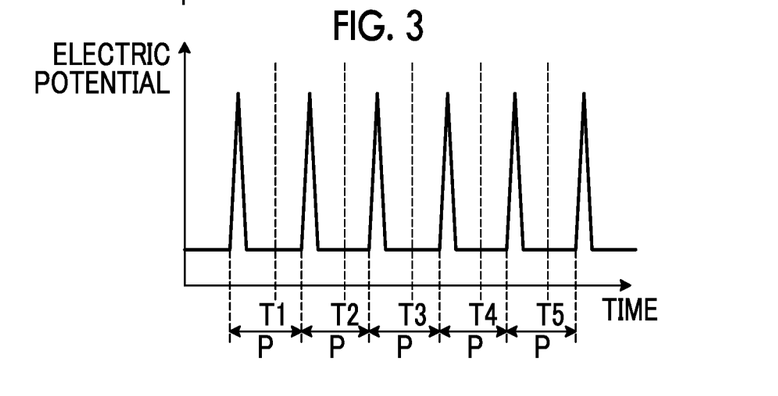
FIG. 3 is a diagram showing an example of the relationship between an electrocardiogram, which is obtained by electrically detecting the pulsation of a myocardial cell group, and a timing at which the same phase is obtained in each period.

The phase information acquisition unit 21 acquires information based on the timing at which the same phase is obtained in each period of the periodic movement of a myocardial cell group or the like. Here, the timing at which the same phase is obtained in each period will be described using an example of the pulsation of a myocardial cell group. FIG. 3 shows an example of the relationship between an electrocardiogram, which is obtained by electrically detecting the pulsation of a myocardial cell group, and a timing at which the same phase is obtained in each period.

As shown in FIG. 3, the electrocardiogram of the myocardial cell group forms a periodic pattern according to the pulsation of the myocardial cell group, but the timing at which the same phase is obtained in each period P of the pattern is, for example, the timing of T1 to T5 shown in FIG. 3.

Then, the phase information acquisition unit 21 of the present embodiment acquires the interval of the timing at which the same phase is obtained. Specifically, the interval of the timing at which the same phase is obtained is the interval of the timing T1 to T2, timing T2 to T3, timing T3 to T4, or timing T4 to T5 shown in FIG. 3. That is, in the case of the present embodiment, information based on the timing at which the same phase is obtained is the same as the period P of the periodic movement.

In the present embodiment, the interval acquired by the phase information acquisition unit 21 is set and input by the user using the input device 2.

Then, the interval acquired by the phase information acquisition unit 21 is output to the control unit 12 of the imaging unit 10, and the control unit 12 determines the imaging timing of the imaging element based on the input interval and controls the imaging element so that each imaging range of the cell group S is imaged at the imaging timing. When determining the imaging timing of the imaging element, the control unit 12 of the present embodiment also considers a movement time required for the imaging unit main body 13 to move between adjacent imaging ranges.

Figure 4:
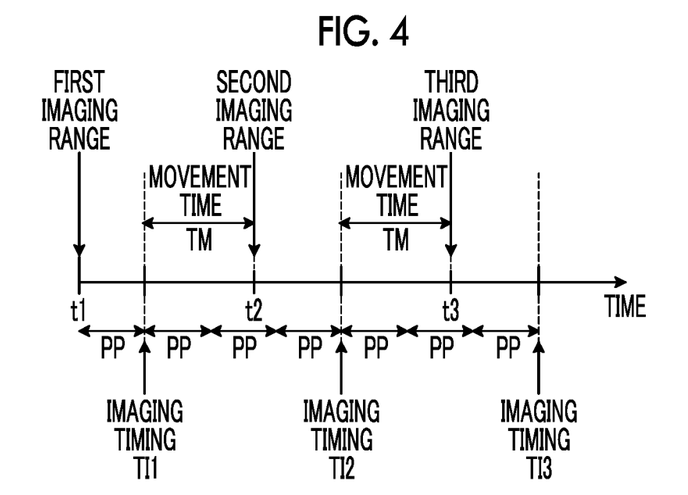
FIG. 4 is a diagram illustrating a method of determining the imaging timing.

Hereinafter, a method of determining the imaging timing in the control unit 12 will be specifically described. FIG. 4 is a diagram illustrating the method of determining the imaging timing. The control unit 12 of the present embodiment determines the timing of an integral multiple of an interval PP of the timing, at which the same phase is obtained, as an imaging timing. At this time, a point in time that is an integral multiple of the interval PP immediately after the movement of the imaging range may be set as the imaging timing. In the present embodiment, the control unit 12 determines the imaging timing with a slight marginal time.

Specifically, first, the control unit 12 determines a point in time when only a time corresponding to the interval PP has passed from a point in time, at which the imaging unit main body 13 is installed in a first imaging range, as the imaging timing TI1 of the first imaging range. Then, a movement time TM for movement from the first imaging range to the second imaging range is added to the imaging timing TI1, and a point in time t2 at which the imaging unit main body 13 is installed in the second imaging range is calculated.

The movement time TM of the imaging range is assumed to be set in advance. Alternatively, the movement time TM of the imaging range may be calculated from the distance between adjacent imaging ranges and the moving speed of the imaging unit main body 13.

Then, the point in time t2 is compared with the timing that is an integral multiple of the interval PP, and the timing of an integral multiple of the interval PP after the point in time t2 is determined as an imaging timing. At this time, in a case where a time between the point in time t2 and the timing, which is an integral multiple of the interval PP immediately after the point in time t2, is short, a subsequent timing of an integral multiple of the interval PP is determined as the imaging timing.

That is, in the case of the example shown in FIG. 4, a timing of an integral multiple after the timing of an integral multiple of the interval PP immediately after the point in time t2 is determined as the imaging timing TI2. Without being limited to the next timing of an integral multiple described above, a point in time obtained by addition of an integral multiple of the interval PP may be set as the imaging timing TI2. For example, a point in time obtained by addition of 2 to 5 times the interval PP may be set as the imaging timing TI2. The imaging timing TI3 of the next third imaging range is determined similarly to the imaging timing TI2 of the second imaging range. By performing imaging at the imaging timing determined in this manner, images with the same phase can be captured for the first to third imaging ranges.

Then, the captured image of each imaging range that has been captured at the imaging timing described above is output to the cell image display control unit 20 so as to be input to the composite image generation unit 22 shown in FIG. 1.

The composite image generation unit 22 generates a composite image by tiling the input captured image of each imaging range. Tiling means arranging the captured images of respective imaging ranges so as to be arranged at positions corresponding to the imaging ranges without gaps. In the present embodiment, since the captured images with the same phase are captured and tilted as described above, it is possible to generate a composite image in which the phase of the periodic movement of the myocardial cell group and the like is the same.

Figure 5:
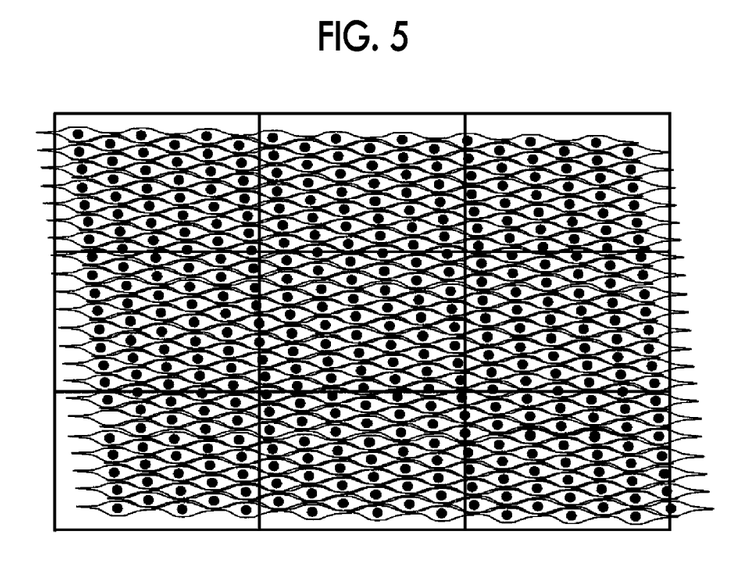
FIG. 5 is a diagram showing an example of a composite image obtained by tiling a plurality of captured images with the same phase.

FIG. 5 shows an example of a composite image. Each rectangular range in FIG. 5 corresponds to each imaging range. By generating a composite image having the same phase in this manner, it is possible to match the shapes of cells at the joint of adjacent captured images. Therefore, it is possible to generate a high-quality composite image as an image to be evaluated.

The composite image generated by the composite image generation unit 22 is output to the display control unit 23 shown in FIG. 1. The display control unit 23 displays the input composite image on the display device 3.

The display device 3 is formed by a display device, such as a liquid crystal display. The input device 2 is formed by an input device, such as a keyboard or a mouse. The display device 3 may be a touch panel, so that the setting input is received by pressing the touch panel screen by the user.

Figure 6:
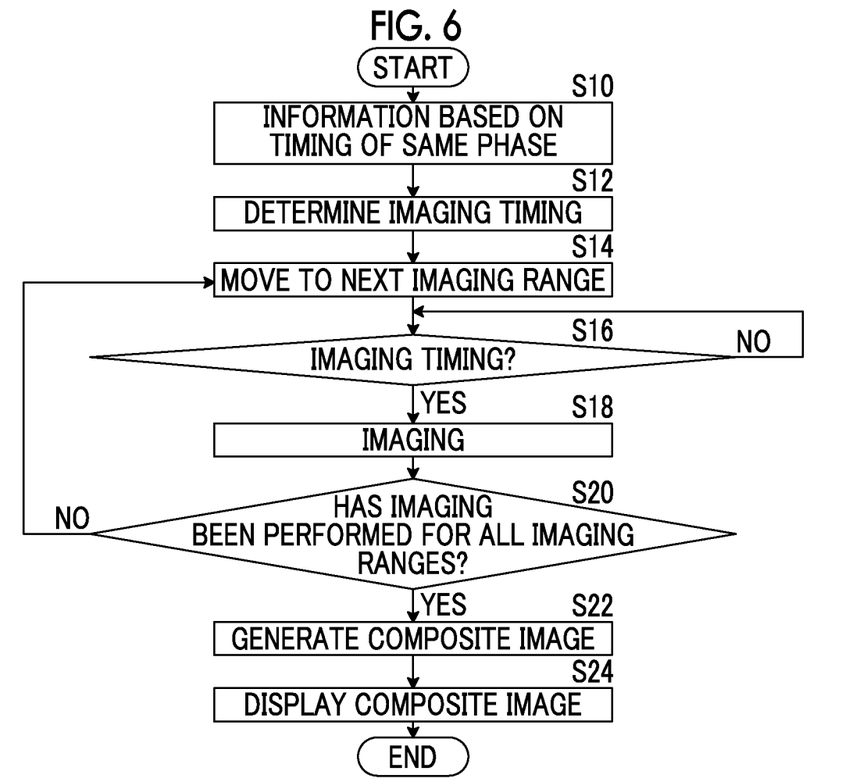
FIG. 6 is a flowchart illustrating the operation of the cell imaging display system using the first embodiment of the cell imaging apparatus of the present invention.

Next, the operation of the cell imaging display system of the present embodiment will be described with reference to the flowchart shown in FIG. 6.

First, the user sets and inputs information based on the timing of the same phase described above using the input device 2 (S10). Specifically, the interval PP of the timing of the same phase is set and input.

The interval PP of the timing of the same phase is acquired by the phase information acquisition unit 21, and the phase information acquisition unit 21 outputs the interval PP to the control unit 12 of the imaging unit 10. Based on the input interval PP, the control unit 12 determines the imaging timing of the captured image of each imaging range (S12).

Then, the imaging unit main body 13 moves to the position of a predetermined imaging range (S14). At the imaging timing of the imaging range (S16, YES), the imaging unit main body 13 captures the imaging range (S18).

Then, the imaging unit main body 13 is transported in the X and Y directions by the X direction transport unit 14 and the Y direction transport unit 15, so that the imaging range is sequentially changed. Accordingly, for each imaging range, imaging is performed at the determined imaging timing (S20, NO). The captured image that has been captured in each imaging range is sequentially output to the composite image generation unit 22 from the imaging unit 10.

Then, when the imaging of all imaging ranges ends (S20, YES), the composite image generation unit 22 generates a composite image by tiling the captured image of each imaging range (S22). The composite image generated by the composite image generation unit 22 is output to the display control unit 23, and the display control unit 23 displays the input composite image on the display device 3 (S24).

Figure 7:
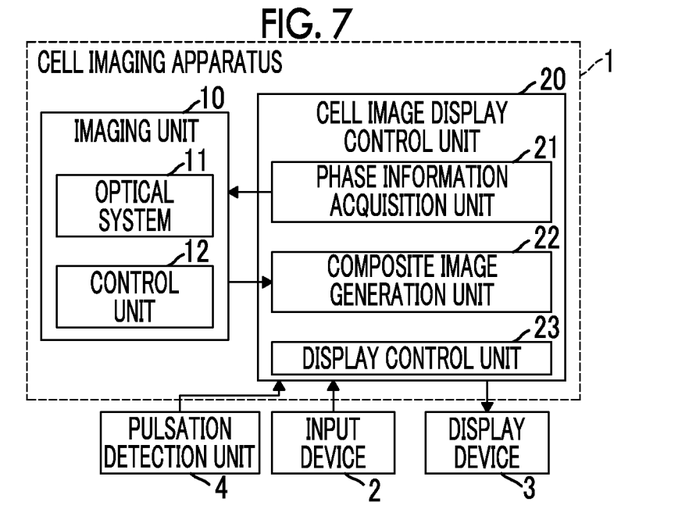
FIG. 7 is a block diagram showing the schematic configuration of a modification example of the cell imaging display system of the first embodiment.

In the cell imaging display system of the embodiment described above, the user sets and inputs the information based on the timing of the same phase using the input device 2. However, without being limited to this, for example, a pulsation detection unit 4 that detects the information of the pulsation of a myocardial cell group may be further provided as shown in FIG. 7, and the phase information acquisition unit 21 may acquire the information of the pulsation detected by the pulsation detection unit 4 and acquire the timing of the same phase from the information of the pulsation. The information of the pulsation detected by the pulsation detection unit 4 is, for example, an electrocardiogram as shown in FIG. 3. As the configuration of the pulsation detection unit 4, for example, electrodes may be provided for the stage T on which the myocardial cell group S to be imaged is placed (refer to FIG. 2), and the electric potential of the myocardial cell group S may be measured by the electrodes.

In the cell imaging display system of the embodiment described above, information based on the timing of the same phase is acquired based on the setting input from the user or the input from the pulsation detection unit 4. However, without being limited to this, for example, imaging may be performed a plurality of times for each imaging range before capturing images with the same phase as described above, and the timing of the same phase may be acquired based on the captured images acquired by the plurality of imaging operations. Hereinafter, a specific example thereof will be described with reference to the flowchart shown in FIG. 8. Also in this case, the schematic configuration of the system is the same as that of the cell imaging display system of the first embodiment shown in FIG. 1.

Figure 8:
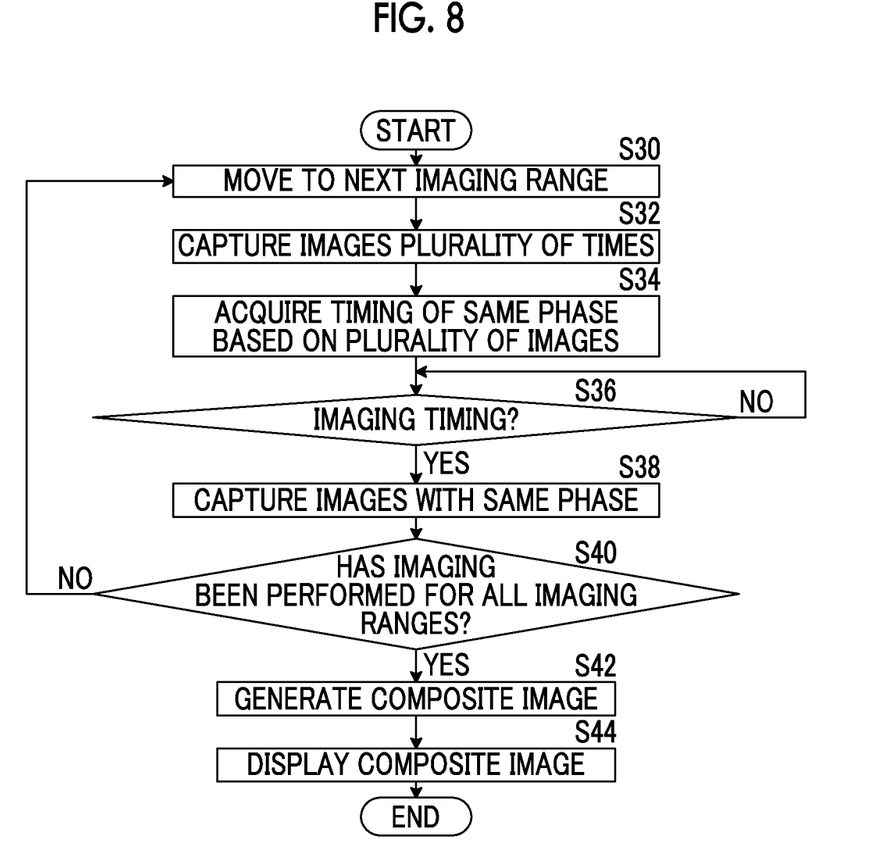
FIG. 8 is a flowchart illustrating the operation of the modification example of the cell imaging display system of the first embodiment.

First, the imaging unit main body 13 moves to the position of a predetermined imaging range (S30). Then, the imaging unit main body 13 performs imaging of a plurality of times for a predetermined period in the imaging range to acquire a plurality of captured images for acquiring the timing of the same phase (S32).

Figure 9:
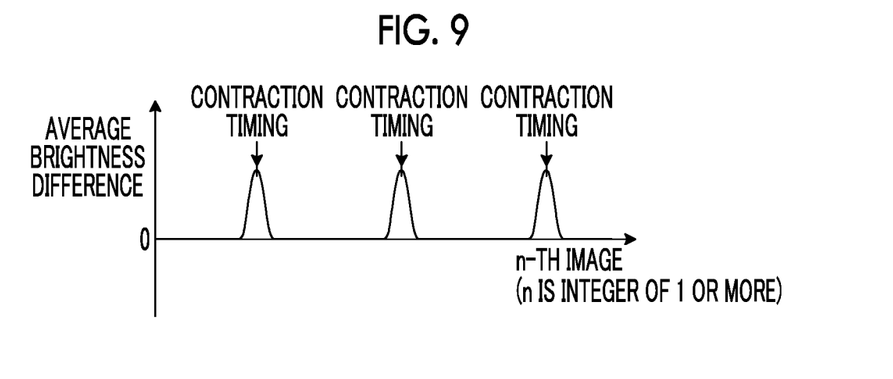
FIG. 9 is a diagram schematically showing a difference in average brightness between respective captured images.

Then, the plurality of captured images for acquiring the timing of the same phase, which have been acquired by the imaging unit main body 13, are acquired by the phase information acquisition unit 21, and the phase information acquisition unit 21 acquires the timing of the same phase based on the plurality of input captured images (S34). Specifically, with a captured image captured first as a reference image, the phase information acquisition unit 21 sequentially calculates a difference between the average brightness of the reference image and the average brightness of the second and subsequent captured images. FIG. 9 is a diagram schematically showing the difference between the average brightness of the reference image and the average brightness of the second and subsequent captured images.

As shown in FIG. 9, the difference in average brightness also changes periodically according to the periodic movement of the myocardial cell group S to be imaged. In particular, in the case of a myocardial cell group, the difference in average brightness at the contraction timing is the largest. Accordingly, the phase information acquisition unit 21 acquires the contraction timing, at which the difference in average brightness is the largest, as the timing of the same phase. The method of determining the contraction timing is not limited to the method of acquiring the difference in average brightness as described above. For example, the contraction timing may be determined by performing binary classification of the average brightness of the captured image for each time using a clustering method, such as K-means. The contraction timing may also be determined by simply determining the average brightness of the captured image for each time using a threshold value.

The information of the timing of the same phase acquired by the phase information acquisition unit 21 is output to the control unit 12 of the imaging unit 10, and the control unit 12 determines any of the input timing of the same phase as an imaging timing (S36, YES), and performs imaging at the imaging timing to acquire a captured image (S38).

Then, the imaging unit main body 13 moves to the next imaging range (S30), and the imaging unit main body 13 performs imaging again a plurality of times for a predetermined period in the next imaging range to acquire a plurality of captured images for acquiring the timing of the same phase (S32). Then, the plurality of captured images for acquiring the timing of the same phase, which have been acquired by the imaging unit main body 13, are acquired by the phase information acquisition unit 21. In the same manner as in the case of the previous imaging range, the phase information acquisition unit 21 determines a contraction timing based on the difference in average brightness between a plurality of input captured images, and acquires the contraction timing as information of the timing of the same phase (S34).

The information of the timing of the same phase acquired by the phase information acquisition unit 21 is output to the control unit 12 of the imaging unit 10, and the control unit 12 determines any of the input timing of the same phase as an imaging timing (S36, YES), and performs imaging at the next imaging timing to acquire a captured image of the next imaging timing (S38).

Then, acquisition of the timing of the same phase based on the plurality of captured images and capturing of images based on the timing are repeatedly performed while moving the imaging range as described above, and the captured images with the same phase are sequentially output to the composite image generation unit 22. Then, when the imaging of all imaging ranges ends (S40, YES), the composite image generation unit 22 generates a composite image by tiling the captured image of each imaging range (S42). The composite image generated by the composite image generation unit 22 is output to the display control unit 23, and the display control unit 23 displays the input composite image on the display device 3 (S44).

In the above explanation, the contraction timing of the myocardial cell group S is acquired as the timing of the same phase. However, the contraction timing may not be necessarily used, and a timing shifted from the contraction timing by a phase set in advance may be acquired as the timing of the same phase. The user may set and input the timing of the same phase arbitrarily using the input device 2. In the present embodiment, the input device 2 corresponds to an in-phase timing receiving unit.

Figure 10:
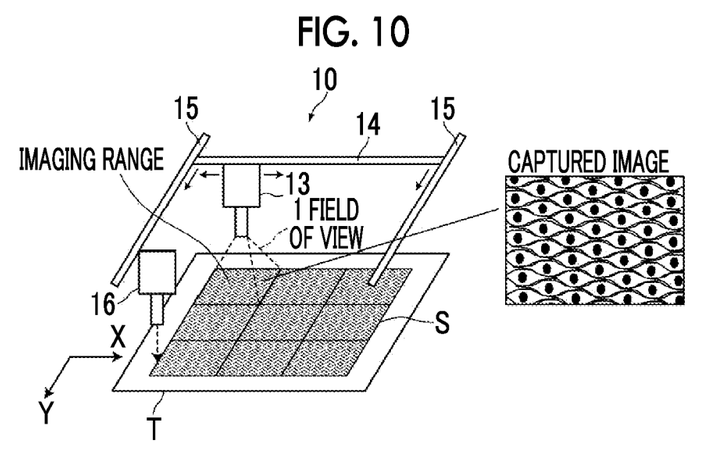
FIG. 10 is a diagram showing an example of the configuration of imaging an edge portion of a cell group.

In the above explanation, the timing of the same phase is acquired based on a plurality of captured images captured for the respective imaging ranges. However, the method of acquiring the timing of the same phase is not limited thereto. For example, as shown in FIG. 10, an edge portion of the myocardial cell group S may be imaged for a predetermined period by a camera 16 for imaging timing acquisition that is separately provided, and the timing of the same phase may be acquired based on the amount of movement of the edge portion.

Specifically, after the imaging unit main body 13 is installed at the position of a predetermined imaging range, the camera 16 images the edge portion of the myocardial cell group S for a predetermined period to acquire a plurality of edge images. The plurality of edge images are sequentially input to the phase information acquisition unit 21, and the phase information acquisition unit 21 detects each edge portion from the plurality of input edge images. Then, with the position of the edge portion of the edge image captured first as a reference position, the phase information acquisition unit 21 calculates a distance of the edge portion, which is detected from each image, from the reference position.

Figure 11:
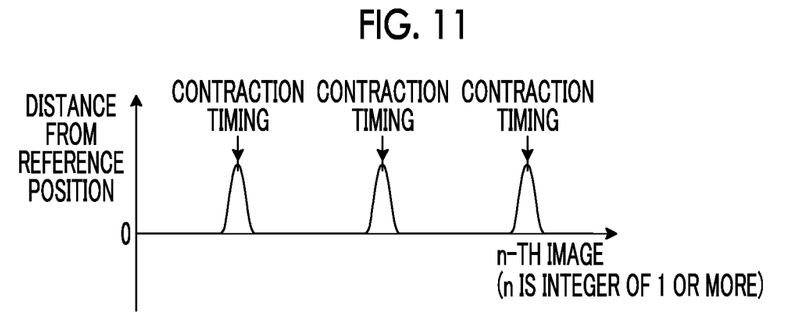
FIG. 11 is a diagram schematically showing a distance of an edge portion of a cell group from the reference position in each captured image.

FIG. 11 is a diagram schematically showing the distance of an edge portion, which is detected from each image, from the reference position. As shown in FIG. 11, the distance of the edge portion from the reference position also changes periodically according to the periodic movement of the myocardial cell group S to be imaged. In the case of the myocardial cell group S, the edge portion of the myocardial cell group S moves the largest at the time of contraction. For this reason, the distance at the contraction timing becomes the largest. Accordingly, the phase information acquisition unit 21 acquires the contraction timing, at which the distance from the reference position becomes the largest, as the timing of the same phase. As a method of determining the contraction timing, for example, the contraction timing may be determined by classifying the distance of the edge portion of each captured image from the reference position according to the K-means method. The contraction timing may also be determined by simply determining the distance from the reference position using a threshold value.

In the same manner as in the above explanation, the information of the timing of the same phase acquired by the phase information acquisition unit 21 is output to the control unit 12 of the imaging unit 10, and the control unit 12 determines any of the input timing of the same phase as an imaging timing, and performs imaging at the imaging timing.

Figure 12:
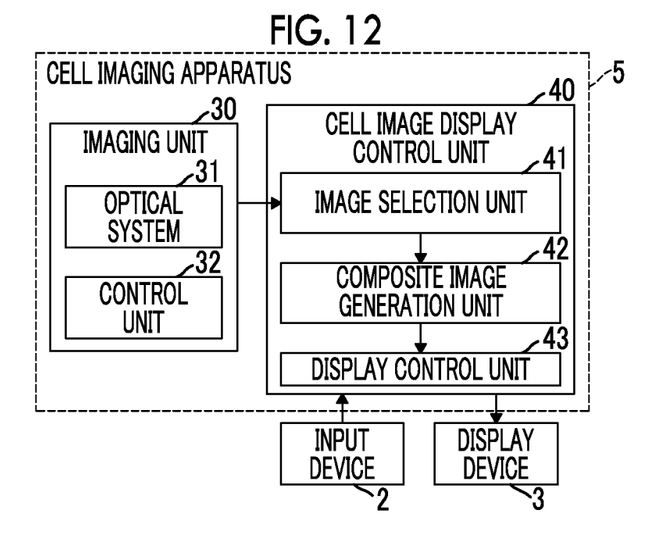
FIG. 12 is a block diagram showing the schematic configuration of a cell imaging display system using a second embodiment of the cell imaging apparatus of the present invention.

Next, a cell imaging display system using a second embodiment of the cell imaging apparatus and method of the present invention will be described. FIG. 12 is a block diagram showing the schematic configuration of the cell imaging display system using the cell imaging apparatus of the present embodiment.

In the cell imaging display system of the first embodiment, the phase information acquisition unit 21 acquires information based on the timing of the same phase as described above, and determines the imaging timing based on the information to acquire captured images with the same phase. In the cell imaging display system of the present embodiment, however, captured images with the same phase are acquired by selecting a captured image of the specific phase among a plurality of captured images that are obtained by performing imaging for a predetermined period for each imaging range.

A cell imaging apparatus 5 of the cell imaging display system of the second embodiment includes an imaging unit 30 and a cell image display control unit 40.

The imaging unit 30 in the cell imaging display system of the second embodiment is different from the imaging unit 10 of the first embodiment in terms of a method of controlling the imaging element and a method of moving the imaging unit main body. The optical system 31, the X direction transport unit 14, and the Y direction transport unit 15 in the imaging unit 30 are the same as those in the first embodiment.

Specifically, a control unit 32 of the present embodiment acquires a plurality of captured images by performing imaging for a predetermined period for each imaging range of the cell group S, and outputs the plurality of captured images to an image selection unit 41 of the cell image display control unit 40.

The cell image display control unit 40 includes the image selection unit 41, a composite image generation unit 42, and a display control unit 43. The image selection unit 41 acquires the plurality of captured images, which have been captured for each imaging range by the imaging unit 30, and selects captured images with the same phase from the acquired captured images.

As a method of selecting images with the same phase in the image selection unit 41, it is preferable to use the same method as the above-described method of acquiring the timing of the same phase based on a plurality of captured images.

That is, with a captured image, which is captured first among a plurality of captured images that are captured for a predetermined imaging range, as a reference image, the image selection unit 41 calculates a difference between the average brightness of the reference image and the average brightness of second and subsequent captured images. Then, the image selection unit 41 selects, for example, captured images between which the difference in average brightness is the largest, as captured images with the same phase. In this case, captured images that are captured at the contraction timing of the myocardial cell group as described above are selected. However, the phase of each captured image to be selected is not limited to the contraction timing, and the user can arbitrarily set the phase of each captured image to be selected using the input device 2 as described above. In the present embodiment, the input device 2 corresponds to an in-phase information receiving unit.

The composite image generation unit 42 acquires the captured images with the same phase that have been selected for the respective imaging ranges by the image selection unit 41, and generates a composite image by tiling the captured images with the same phase. The display control unit 43 displays the input composite image on the display device 3. The input device 2 and the display device 3 are the same as those in the first embodiment described above.

Figure 13:
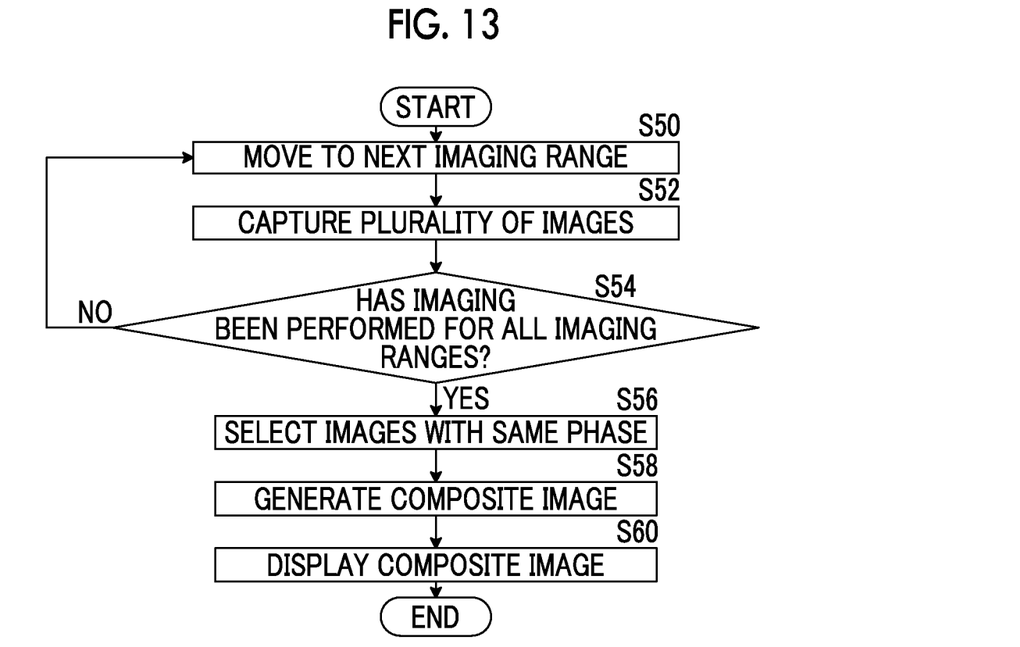
FIG. 13 is a flowchart illustrating the operation of the cell imaging display system using the second embodiment of the cell imaging apparatus of the present invention.

Next, the operation of the cell imaging display system of the present embodiment will be described with reference to the flowchart shown in FIG. 13.

First, the imaging unit main body 13 moves to the position of the first imaging range under the control of the control unit 32 (S50), and performs imaging for a predetermined period for each imaging range to acquire a plurality of captured images (S52).

Then, the imaging unit main body 13 is transported in the X and Y directions by the X direction transport unit 14 and the Y direction transport unit 15, so that the imaging range is sequentially changed. Accordingly, for each imaging range, a plurality of captured images are acquired (S54, NO).

Then, after the capturing of a plurality of images for all imaging ranges ends (S54, YES), the image selection unit 41 selects captured images with the same phase among the plurality of captured images that have been captured for each imaging range (S56).

The captured images with the same phase selected for each imaging range by the image selection unit 41 are output to the composite image generation unit 42, and the composite image generation unit 22 generates a composite image by tiling the captured images with the same phase of each imaging range (S58). The composite image generated by the composite image generation unit 22 is output to the display control unit 43, and the display control unit 43 displays the input composite image on the display device 3 (S60).

In the cell imaging display system of the second embodiment described above, captured images with the same phase are selected based on the difference in average brightness between the plurality of captured images. However, the method of selecting captured images with the same phase is not limited thereto. For example, as described in the first embodiment, an edge portion of a cell group may be imaged by the camera 16 separately provided, and captured images with the same phase may be selected based on the amount of movement of the edge portion. Specifically, the imaging period of a plurality of captured images in each imaging range and the distance of the edge portion from the reference position shown in FIG. 11 may be associated with each other, and captured images that are captured at the contraction timing shown in FIG. 11 may be selected as images with the same phase.

Figure 14:
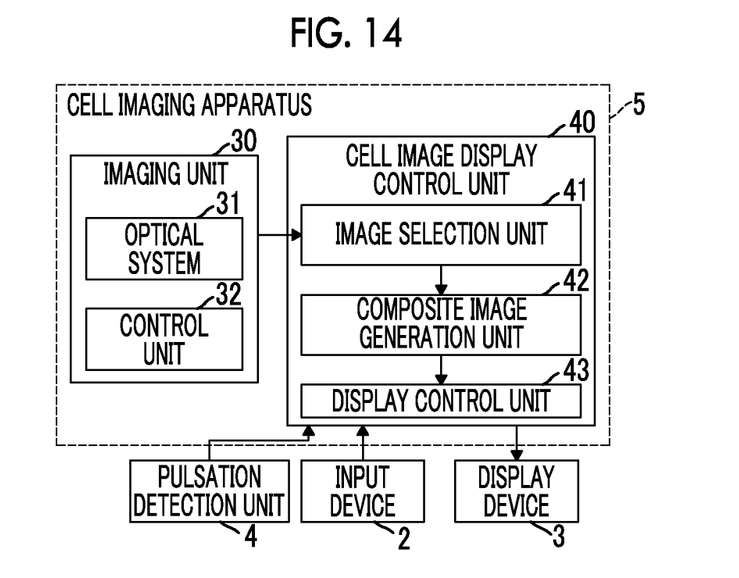
FIG. 14 is a block diagram showing the schematic configuration of a modification example of the cell imaging display system of the second embodiment.

As in the first embodiment, a pulsation detection unit 4 may be provided as shown in FIG. 14, and captured images with the same phase may be selected based on the electrocardiogram acquired by the pulsation detection unit 4. Specifically, for example, the imaging period of a plurality of captured images in each imaging range and the electrocardiogram shown in FIG. 3 may be associated with each other, and captured images that are captured at the timing of the peak shown in FIG. 3, that is, the contraction timing of myocardial cell group, may be selected as images with the same phase.

In the cell imaging display systems of the first and second embodiments, the phase of a captured image to be combined can be set arbitrarily as described above. However, in a case where the object to be imaged is a myocardial cell group, it is desirable that the phase of the captured image to be combined is the contraction timing and the relaxation timing of the pulsating movement.

For example, in the case of the cell imaging display system of the first embodiment, the phase information acquisition unit 21 acquires both the contraction timing and the relaxation timing, and the imaging unit 10 captures an image at both the contraction timing and the relaxation timing for each imaging range. In the cell imaging display system of the first embodiment described above, in a case where the timing of an integral multiple of the interval PP is set as an imaging timing, the timing at the start of imaging may be set to the contraction timing and the relaxation timing.

Then, it is preferable that the composite image generation unit 22 generates a first composite image by arranging the captured image at the contraction timing of each imaging range and generates a second composite image by arranging the image at the relaxation timing of each imaging range and that the display control unit 23 displays the first and second composite images side by side on the display device 3.

The first and second composite images may be translucently processed, and the translucently processed first and second composite images may be displayed on the display device 3 so as to overlap each other.

In the case of the cell imaging display system of the second embodiment, the image selection unit 41 selects both the captured image at the contraction timing and the captured image at the relaxation timing for each imaging range.

Then, it is preferable that the composite image generation unit 22 generates a first composite image by arranging the captured image at the contraction timing of each imaging range and generates a second composite image by arranging the image at the relaxation timing of each imaging range and that the display control unit 23 displays the first and second composite images on the display device 3.

By comparing the first composite image at the contraction timing with the second composite image at the relaxation timing as described above, it is possible to evaluate the function or quality of the myocardial cell group.

In the cell imaging display system of the second embodiment described above, a motion picture may be captured by performing imaging at a predetermined frame rate for each imaging range, and a composite image of one frame may be generated by selecting and tilting images of the same phase frame from the motion picture captured for each imaging range. Similarly, a motion picture of a composite image may be generated and displayed by generating a composite image for each phase.

EXPLANATION OF REFERENCES 1, 5: cell imaging apparatus
2: input device
3: display device
4: pulsation detection unit
10, 30: imaging unit
11, 31: optical system
12, 32: control unit
13: imaging unit main body
14: X direction transport unit
15: Y direction transport unit
16: camera
20, 40: cell image display control unit
21: phase information acquisition unit
22, 42: composite image generation unit
23, 43: display control unit
41: image selection unit

What is claimed is:

1. A cell imaging apparatus, comprising:
an imager that images a cell group including a plurality of periodically moving cells while changing an imaging range; and
a controller configured to:
acquire information based on a timing of the same phase in each period of the periodic movement; and
generate a composite image by arranging images of the respective imaging ranges,
wherein the imager captures images with the same phase for the respective imaging ranges on the basis of the information based on the timing of the same phase, and
the controller is further configured to generate the composite image by arranging the images with the same phase,
wherein the cell group is a myocardial cell group,
a pulsation detector that detects a pulsation, which is periodic movement of the myocardial cell group, is provided,
the controller is further configured to acquire the information, which is based on the timing of the same phase, based on information of the pulsation, and
the controller is further configured to generate a composite image in which the phase of the periodic movement of the myocardial cell group is the same.

2. The cell imaging apparatus according to claim 1, wherein the controller is further configured to receive a setting input of a timing of the same phase.

3. The cell imaging apparatus according to claim 1, wherein the imager performs imaging of a plurality of times for each imaging range before capturing the images with the same phase, and
the controller is further configured to acquire the information, which is based on the timing of the same phase, based on images acquired by the plurality of imaging operations.

4. The cell imaging apparatus according to claim 2, wherein the imager performs imaging of a plurality of times for each imaging range before capturing the images with the same phase, and
wherein the controller is further configured to acquire the information, which is based on the timing of the same phase, based on images acquired by the plurality of imaging operations.

5. The cell imaging apparatus according to claim 1,
wherein the cell group is a myocardial cell group, and
the controller is further configured to acquire a contraction timing or a relaxation timing in pulsation of the myocardial cell group.

6. The cell imaging apparatus according to claim 2,
wherein the cell group is a myocardial cell group, and
the controller is further configured to acquire a contraction timing or a relaxation timing in pulsation of the myocardial cell group.

7. The cell imaging apparatus according to claim 5,
wherein the controller is further configured to acquire both the contraction timing and the relaxation timing,
the imager captures an image at both the contraction timing and the relaxation timing for each imaging range, and
the controller is further configured to generate a first composite image by arranging images at the contraction timing of each imaging range, and generates a second composite image by arranging images at the relaxation timing of each imaging range.

8. The cell imaging apparatus according to claim 1,
wherein the imager determines an imaging timing of the image based on information regarding a predetermined movement time for movement between the imaging ranges adjacent to each other and the information regarding the timing of the same phase.

9. A cell imaging method using the cell imaging apparatus according to claim 1 for imaging a cell group including a plurality of periodically moving cells while changing an imaging range, comprising:
acquiring information based on a timing of the same phase in each period of the periodic movement;
capturing images with the same phase for the respective imaging ranges on the basis of the information based on the timing of the same phase, and
generating a composite image by arranging the images with the same phase of the respective imaging ranges.

10. A cell imaging apparatus, comprising:
an imager that images a cell group, which includes a plurality of periodically moving cells, a plurality of times for each imaging range while changing an imaging range; and
a controller configured to:
select images with the same phase in each period of the periodic movement from a plurality of images acquired by a plurality of imaging operations in each imaging range; and
generate a composite image by arranging the images with the same phase that are selected,
wherein the cell group is a myocardial cell group,
a pulsation detector that detects a pulsation, which is periodic movement of the myocardial cell group, is provided,
the controller selects the images with the same phase based on information of the pulsation, and
the controller generates a composite image in which the phase of the periodic movement of the myocardial cell group is the same.

11. The cell imaging apparatus according to claim 10,
wherein the controller is further configured to receive designation of the same phase in each period of the periodic movement.

12. The cell imaging apparatus according to claim 10,
wherein the controller is further configured to select the images with the same phase based on images acquired by the plurality of imaging operations.

13. The cell imaging apparatus according to claim 11,
wherein the controller is further configured to select the images with the same phase based on images acquired by the plurality of imaging operations.

14. The cell imaging apparatus according to claim 10,
wherein the cell group is a myocardial cell group, and
the controller is further configured to select an image captured at a contraction timing or an image captured at a relaxation timing in pulsation of the myocardial cell group.

15. The cell imaging apparatus according to claim 14,
wherein the controller is further configured to:
select both an image captured at the contraction timing and an image captured at the relaxation timing for each imaging range, and
generate a first composite image by arranging images at the contraction timing of each imaging range, and generates a second composite image by arranging images at the relaxation timing of each imaging range.

16. A cell imaging method using the cell imaging apparatus according to claim 10, comprising:
imaging a cell group, which includes a plurality of periodically moving cells, a plurality of times for each imaging range while changing an imaging range;
selecting images with the same phase in each period of the periodic movement from a plurality of images acquired by a plurality of imaging operations in each imaging range; and
generating a composite image by arranging the selected images with the same phase.

* * * * *